(12) United States Patent
Andrews et al.

(10) Patent No.: US 7,662,863 B2
(45) Date of Patent: Feb. 16, 2010

(54) THERAPEUTIC AGENT FOR THE USE IN REDUCING ALCOHOL INTOXICATION AND REDUCING OR ELIMINATING THE NEGATIVE SIDE EFFECTS ASSOCIATED WITH ALCOHOL INGESTION

(76) Inventors: Alan Andrews, 8909 Beatty Ct., Austin, TX (US) 78749; Christine Fields, 1125 Oxford La., Lake Zurich, IL (US) 60047; Allison Minton, 8905 Hachita Dr., Austin, TX (US) 78749; Brian Slaga, 3509 Golfview Dr., Key West, FL (US) 33040; Sean Traci, 1810 Elmwood Ave., Wilmette, IL (US) 60091; Loretta Zapp, 6367 Clearview Rd., Boulder, CO (US) 80303

( * ) Notice: Subject to any disclaimer, the term of this patent is extended or adjusted under 35 U.S.C. 154(b) by 201 days.

(21) Appl. No.: 10/458,764

(22) Filed: Jun. 9, 2003

(65) Prior Publication Data

US 2004/0248818 A1  Dec. 9, 2004

(51) Int. Cl.
*A01N 31/00* (2006.01)
*A01N 37/00* (2006.01)
*A61K 31/045* (2006.01)
*A61K 31/19* (2006.01)
*C07H 1/00* (2006.01)
*C07C 61/00* (2006.01)
*C07C 61/08* (2006.01)

(52) U.S. Cl. ............ 514/724; 514/557; 536/1.11; 562/400

(58) Field of Classification Search ........... 514/460, 514/724, 557; 536/1.11; 562/400
See application file for complete search history.

(56) References Cited

U.S. PATENT DOCUMENTS

| 4,027,017 | A | * | 5/1977 | Hata et al. | ............ 514/51 |
| 4,058,601 | A | | 11/1977 | Hata et al. | |
| 4,165,376 | A | * | 8/1979 | Rosenberg | ........... 514/325 |
| 4,845,123 | A | * | 7/1989 | Walaszek et al. | ......... 514/473 |
| 5,712,309 | A | | 1/1998 | Finnin et al. | |
| 5,888,532 | A | | 3/1999 | Pritsos et al. | |
| 6,045,819 | A | | 4/2000 | Takebe | |
| 6,077,838 | A | | 6/2000 | Hausheer | |
| 6,245,360 | B1 | | 6/2001 | Markowitx | |
| 2001/0000472 | A1 | | 4/2001 | Henderson et al. | |
| 2001/0043956 | A1 | | 11/2001 | Mirza et al. | |
| 2002/0006910 | A1 | | 1/2002 | Miasnikov | |
| 2002/0142991 | A1 | | 10/2002 | Herzenberg et al. | |
| 2002/0155103 | A1 | | 10/2002 | Crippen | |

FOREIGN PATENT DOCUMENTS

| CN | 1291499 | * | 10/2000 |
| JP | 52072836 | * | 6/1977 |
| JP | 2160589 | | 6/1990 |
| RU | 2 012 350 | | 5/1994 |

OTHER PUBLICATIONS (no. authors given), "Calcium-D-Glucrate". Alternative Medicine Review 2002, 7, 336-339.*
Kamil, I. A.; Smith, J. N.; Williams, R. T. Biochemistry 1953, 53, 129-136.*
Dutton et al. (Biochem, V 64(4), Dec. 1956, p. 693-701).*
Ritz et al. (Z.ges exp.Med 153, 237-245 1970).*
Walaszek et al. (Nutrition Research, vol. 16, 4, pp. 673-681, 1996).*
Dwivedi et al., "Effect of Calcium Glucarate on β-Glucuronidase Activity and Glucarate Content of Certain Vegetables and Fruits," *Biochemical Medicine and Metabolic Biology*, 1990; 43:83-92.
Walaszek et al., "Metabolism, Uptake, and Excretion of a D-Glucaric Acid Salt and its Potential Use in Cancer Prevention," *Cancer Detection and Prevention*, 1997; 2(2):178-190.
Walaszek et al., "Repression by Sustained-Release β-Glucuronidase Inhibitors of Chemical Carcinogen-Mediated Induction of a Marker Oncofetal Protein in Rodents," *Journal of Toxicology and Environmental Health*, 1988; 23:15-27.
Wiese et al., "The Alcohol Hangover," *Annals of Internal Medicine*, 2000; 132(11):897-902.

* cited by examiner

*Primary Examiner*—Sreeni Padmanabhan
*Assistant Examiner*—Umamaheswari Ramachandran
(74) *Attorney, Agent, or Firm*—Patton Boggs LLP

(57) ABSTRACT

A therapeutic method and associated compound for ameliorating alcohol intoxication and preventing and/or reducing hangover symptoms. Glucaric acid, any salt thereof, and/or any derivative or metabolized form thereof is provided in therapeutic dosage, before and/or after the intake of alcohol.

6 Claims, 3 Drawing Sheets

FIG. 1

|   | Sex | Weight | Ounces Alcohol Consumed | Duration | BAC 1 | BAC 2 | BAC 3 | BAC 4 |
|---|---|---|---|---|---|---|---|---|
| 1 | M | 220 | 4.608 | 6 | 0.15 | 0.03 | 0.17 | 0.05 |
| 2 | M | 207 | 4.224 | 6 | 0.13 | 0.01 | 0.16 | 0.04 |
| 3 | M | 198 | 4.608 | 6 | 0.15 | 0.03 | 0.18 | 0.06 |
| 4 | F | 142 | 3.456 | 6 | 0.17 | 0.05 | 0.21 | 0.05 |
| 5 | M | 195 | 3.456 | 6 | 0.12 | 0 | 0.14 | 0.02 |
| 6 | F | 123 | 1.92 | 5 | 0.1 | 0 | 0.12 | 0.02 |
| 7 | F | 110 | 1.92 | 5 | 0.1 | 0 | 0.13 | 0.03 |
| 8 | M | 187 | 3.072 | 5 | 0.11 | 0.01 | 0.13 | 0.03 |
| 9 | M | 196 | 3.84 | 5 | 0.12 | 0.02 | 0.15 | 0.05 |
| 10 | M | 185 | 3.456 | 5 | 0.11 | 0.01 | 0.14 | 0.04 |
| 11 | M | 234 | 2.688 | 4 | 0.08 | 0 | 0.09 | 0.01 |
| 12 | F | 154 | 1.536 | 4 | 0.08 | 0 | 0.09 | 0.01 |
| 13 | F | 165 | 1.92 | 4 | 0.08 | 0 | 0.1 | 0.02 |
| 14 | M | 215 | 2.688 | 4 | 0.08 | 0 | 0.1 | 0.02 |
| 15 | F | 128 | 3.072 | 6 | 0.17 | 0.05 | 0.21 | 0.07 |
| 16 | M | 212 | 3.84 | 6 | 0.12 | 0 | 0.14 | 0.02 |
| 17 | M | 202 | 4.224 | 6 | 0.13 | 0.01 | 0.16 | 0.04 |
| 18 | F | 117 | 2.688 | 6 | 0.16 | 0.04 | 0.2 | 0.06 |
| 19 | F | 135 | 3.072 | 6 | 0.16 | 0.04 | 0.2 | 0.06 |
| 20 | F | 138 | 3.456 | 6 | 0.18 | 0.06 | 0.22 | 0.1 |
| Sum |   |   |   |   | 2.5 | 0.36 | 3.04 | 0.8 |
| Average |   |   |   |   | 0.125 | 0.018 | 0.152 | 0.04 |
| % Change |   |   |   |   | 17.8% | 55.0% |   |   |

BAC = Blood Alcohol Content
BAC 1 = After alcohol consumption with Glucarate administered
BAC 2 = 8 hours after alcohol consumption with Glucarate administered
BAC 3 = After alcohol consumption with Placebo administered
BAC 4 = 8 hours after alcohol consumption with Placebo administered

FIG. 2

Glucarate Administered

|  | 1 | 2 | 3 | 4 | 5 |
|---|---|---|---|---|---|
| Headache | Ī | Ī | Ī | ● | Ī |
| Dizziness | Ī | Ī | Ī | Ī | ● |
| Nausea | Ī | Ī | Ī | Ī | ● |
| Dehydration | Ī | Ī | ● | Ī | Ī |
| Fatigue | Ī | Ī | Ī | ● | Ī |
| Cotton Mouth | Ī | Ī | Ī | ● | Ī |
| Stressed | Ī | Ī | Ī | Ī | ● |

Placebo Administered

|  | 1 | 2 | 3 | 4 | 5 |
|---|---|---|---|---|---|
| Headache | Ī | ● | Ī | Ī | Ī |
| Dizziness | Ī | Ī | ● | Ī | Ī |
| Nausea | Ī | ● | Ī | Ī | Ī |
| Dehydration | ● | Ī | Ī | Ī | Ī |
| Fatigue | Ī | ● | Ī | Ī | Ī |
| Cotton Mouth | ● | Ī | Ī | Ī | Ī |
| Stressed | Ī | Ī | ● | Ī | Ī |

FIG. 3

Glucarate

|  | 1 | 2 | 3 | 4 | 5 |
|---|---|---|---|---|---|
| Mood | Ī | Ī | Ī | ● | Ī |
| Appearance | Ī | Ī | ● | Ī | Ī |
| Health | Ī | Ī | Ī | Ī | ● |

Placebo

|  | 1 | 2 | 3 | 4 | 5 |
|---|---|---|---|---|---|
| Mood | Ī | ● | Ī | Ī | Ī |
| Appearance | Ī | ● | Ī | Ī | Ī |
| Health | Ī | Ī | ● | Ī | Ī |

THERAPEUTIC AGENT FOR THE USE IN REDUCING ALCOHOL INTOXICATION AND REDUCING OR ELIMINATING THE NEGATIVE SIDE EFFECTS ASSOCIATED WITH ALCOHOL INGESTION

BACKGROUND OF THE INVENTION

1. Field of the Invention

The present invention relates to methods and compositions for addressing the symptoms of intoxication or "hangover."

2. Background Information

A. General Systemic Alcohol Reactions and Processes.

Alcohol intoxication and the subsequent hangover are accompanied by the development of a number of subjective and objectively observable symptoms: sensation of discomfort, inadequacy of perception, headache, disturbances in the formation of long-term memory, thirst, apathy (sometimes hyperactivity), agitation which gives way to depression, disturbances in the coordination of movements, reduction of the response rate, and many other deviations, differing in seriousness, of psychological, physiological and somatic character as well as the obvious overall increase in blood alcohol content.

Once ingested, ethanol is rapidly absorbed from the upper gastrointestinal tract. The majority is then oxidized, primarily in the liver; only 2 to 10% is eliminated in urine and breath. Three pathways exists for alcohol metabolism: the alcohol dehydrogenase (ADH) pathway in the cytosol; the microsomal ethanol oxidizing system (MEOS) located in the smooth endoplasmic reticulum and the catalase pathway located in peroxisomes. ADH, which exists in multiple molecular forms, catalyses the conversion of ethanol to acetaldehyde. MEOS activity has now been attributed to CYP2E1, an isoform of cytochrome P450. Its role in ethanol metabolism in non-habitual drinkers is probably small, at least when circulating ethanol concentrations are low. Catalase does not appear to play a major role in ethanol oxidation, at least under physiological conditions.

The major route of metabolism of ethyl alcohol is its oxidation in the liver catalyzed by the cytosolic enzyme alcohol dehydrogenase (ADH). It catalyzes the following reaction:

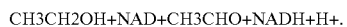

$$CH_3CH_2OH + NAD \rightarrow CH_3CHO + NADH + H+.$$

This reaction produces acetaldehyde, a highly toxic substance. ADH has broad specificity, catalyzing various alcohols and steroids and catalyzing the oxidation of fatty acids. It also is not a solitary enzyme in that there are five different ADH genes, two of which ADH2 and ADH3 shown polymorphism (variations). Of importance is the fact that the ability of people to oxidize ethyl alcohol is dependent upon the genetic makeup of the individual.

The second step of the ADH metabolism is catalyzed by acetaldehyde dehydrogenase. This enzyme converts acetaldehyde to acetic acid, which is a normal metabolite in humans and hence is non-toxic.

Another system in the liver which oxidizes ethanol via the enzyme cytochrome P450IIE1 (CYP2E1) is called the MEOS system. The reaction catalyzed by MEOS is:

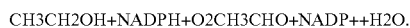

$$CH_3CH_2OH + NADPH + O_2 \rightarrow CH_3CHO + NADP+ + H_2O.$$

Though of minor significance in comparison to ADH metabolism of alcohols, the MEOS system seems to play an increasingly important role at higher concentrations of ethanol. It is not surprising that there are variations in the P450E1 enzyme that lead to differences in the rate of alcohol metabolism. This may have implications for tissue damage from ethanol, particular in the liver.

Peak blood alcohol concentrations are attained approximately one hour after ingestion. A number of factors influence the levels attained, including the speed at which the beverage was drunk, whether it was consumed together with food, the rate of gastric emptying and body habits.

Women attain consistently higher blood alcohol concentrations than men following a standard oral dose of alcohol because their body water, and hence the compartment in which the alcohol distributes, is significantly smaller than in men. Alcohol is eliminated from the body at a rate of 7 to 10 g (1 unit) an hour. Blood alcohol concentrations may, therefore, remain elevated for considerable periods following ingestion. Thus, if an individual imbibes 6 pints of premium strength beer (18 units) during an evening, then alcohol will still be detectable in their blood at 11.00 a.m. the following day.

The rate limiting factor in the metabolism of alcohol is the dissociation of the NADH-ADH enzyme complex. The ADH-mediated oxidation of ethanol results in transfer of hydrogen to the co-factor NAD converting it to its reduced form NADH. The rate of alcohol oxidation is, therefore, determined by the capacity of the liver to re-oxidize NADH. Chronic alcohol misuse is associated with an increase in the metabolic rate for alcohol as a result of induction of the MEOS system; under these circumstances this alternative pathway can account for up to 10% of ethanol oxidation.

The liver is the primary detoxification organ and plays several roles in removing unwanted substances from the body. It filters the blood to remove large toxins, synthesizes and secretes bile full of cholesterol and other fat-soluble toxins and enzymatically disassembles unwanted chemicals. This enzymatic process typically occurs within two different stages referred to as Phase I and Phase II detoxification.

Due to the vast amount of literature indicating that alcohol metabolism happens via the ADH, or secondarily the cytochrome P450IIE01 (MEOS) enzymes, it is clear that alcohol and other drugs typically activate the bodies Phase I detoxification systems. In Phase I detoxification the liver is the primary organ responsible for the removal of the unwanted toxin via a two-step enzymatic process for the neutralization of unwanted chemical compounds. In the case of alcohol it is converted first to acetaldehyde, then to acetic acid for excretion.

B. Present Measures for Addressing Hangovers.

Today, the range of available treatment options for minimizing or eliminating alcohol intoxication and alcohol withdrawal syndrome, commonly known as a "hangover," is extremely limited. According to articles published in the Annals of Internal Medicine ("Alcohol Hangover" Jun. 6, 2000, Volume 132 Number 11), The New York Times ("Morning-After Pill for Hangovers?" Dec. 27, 2000), there are currently no products on the U.S. market that could minimize alcohol intoxication and prevent hangovers—or at least treat the symptoms effectively and quickly.

Widely known is the ALKA-SELTZER preparation, one tablet of which comprises 0.324 of acetylsalicylic acid as the active component, 0.965 g of citric acid as an auxiliary ingredient, and 1.625 g of sodium bicarbonate which neutralizes acids with the evolution of carbon dioxide gas on dissolution and provides for an "effervescence" effect of the resultant drink (source: loose leaf instructions for use of the ALKA-SELTZER medicinal preparation manufactured by Miles Corp., Great Britain). This preparation, through action of the acetylsalicylic acid, inhibits the penetration of toxins into the brain, lowers the intercranial pressure, and mitigates headache. Nevertheless, the ALKA-SELTZER preparation does not eliminate the main manifestations of alcohol intoxication and does not restore the capacity for work.

One method for allaying drunkenness is known in the art (RU Pat. No. 2012350, IPC: A61 K 35/78, 1994), which involves the administration of 20 drops of an alcoholic peppermint tincture, 2 drops of mint oil, 1 g of succinic acid, and 10 g of sugar or fructose, all in a water base. This preparation can only partially eliminate the consequences of intoxication.

Several other chemical compounds or compositions are claimed to have some efficacy in removing alcohol and decreasing the negative symptoms associated with alcohol consumption. An example is shown in US Application No. 20020155103, and is based upon activated charcoal or limestone which is used to absorb the alcohol prior to absorption into the bloodstream. US Patent Application No. 20010043956 teaches the primary active ingredients of ephedrine and charcoal. U.S. Pat. No. 5,888,532 teaches nicotinamide-adenine dinucleotide phosphate derivatives. The invention of U.S. Pat. No. 6,077,838 utilizes thiol or reducible disulfide compounds. U.S. Pat. No. 5,712,309 teaches incorporating effective amounts of L-methionine and L-alanine. US Application No. 20020142991 teaches the administering of key ingredient N-acetylcysteine, while US Application No. 20010000472 shows a composition containing L-ergothioneine, milk thistle and s-adenosylmethionne, all active ingredients claimed to decrease the level of circulating acetaldehyde.

Additional patents exists which target the specific malnutrition aspects of alcohol intoxication as referred to in U.S. Pat. No. 6,045,819 which incorporates koji mold and U.S. Pat. No. 6,245,360, which is an extended release multivitamin with several minerals and trace elements such as thiamine and folic acid.

C. Principles and Theories Underlying the Present Invention.

Phase I detoxification aides in the removal of toxins within our system faster than any other detoxification mechanism. This is the primary method our body utilizes to quickly remove alcohol from the blood stream. Phase II detoxification involves a process called conjugation, in which various enzymes in the liver attach small chemicals to the toxin to either neutralize the toxin or make it more easily excreted via the urine or bile. One of the six Phase II detoxification pathways is glucuronidation.

Glucuronidation combines glucuronic acid with the toxin for removal and requires the enzyme UDP-glucuronyl transferase (UDPGT) for activation. The literature cites many prescribed drugs and hormones detoxified through this primary pathway.

In order to work efficiently, the Phase II enzymes, like UDPGT, need nutrients, both for their activation and to provide the small molecules they add to the toxin. The nutrient specific for Glucuronidation is glucuronic acid. Glucuronic acid is reacted in vivo to form many other compounds such as glucaric acid, D-glucaro-1,4-lactone and D-glucaro-6,3-lactone.

It has been speculated, because glucuronidation is effective at the removal of excess hormones within the human blood plasma, that during alcohol consumption perhaps some of the alcohol being consumed, then absorbed by the blood to eventually be filtered by the liver can ultimately be removed via conjugation of glucuronic acid.

SUMMARY OF THE INVENTION

It is an object of the present invention to provide an improved method and associated medicament which is useful in preventing or addressing existing conditions associated with excess alcohol consumption.

The present invention employs active ingredient(s) that can be derived from an all-natural source, or produced synthetically to aide in alcohol detoxification in the body. An increase or boost in detoxification can reduce or eliminate the side effects associated with alcohol consumption such as dizziness, nausea, headache, dry-mouth, fatigue, etc. Conventional methods typically employ activated carbon to essentially absorb the alcohol, enzymes to increase alcohol breakdown in the body or acetaldehyde removal. No such supplement or product exists which can increase the detoxification of alcohol via a Phase II glucuronidation pathway in the body to alleviate the symptoms of a hangover.

BRIEF DESCRIPTION OF THE DRAWINGS

FIG. 1 is a table showing individual parameters of test subjects.

FIG. 2 is a table showing subject assessments of hangover specific symptoms after either glucarate or placebo treatment.

FIG. 3 is a table showing subject assessments of over-all well-being factors after either glucarate or placebo treatment.

DETAILED DESCRIPTION OF THE PREFERRED EMBODIMENT

The above-referenced theory pertaining to conjugation of glucuronic acid was the subject of the present inventors' testing. An oral dosage of a glucarate salt was proposed to increase the body's overall ability to enhance glucuronidation.

A salt of glucarate acid, either potassium or calcium in this case, once ingested is converted to D-glucaro-1,4-lactone, a primary compound of glucuronic acid. The overall increase in glucuronic acid enhanced the body's ability to increase glucuronidation was of little surprise to the present researchers. However, effect of the increase in glucuronic acid in increasing the body's ability to remove blood alcohol content (BAC) represents a significant discovery. The increase in glucuronidation activity not only allowed a lowering of BAC over a period of time, but also had a positive effect on the non-acute symptoms typically associated with alcohol consumption such as headaches, nausea, mild depression, body aches, etc.

Although the exact mechanism in not clearly understood one can deduce that, once entered into the liver, the alcohol, or the bi-products of alcohol metabolism such as acetaldehyde, can be conjugated with glucuronic acid and removed from the body just as they can with other primary excretion pathways. Further, the alcohol or bi-products may even have an affinity for this specific conjugation.

In view of the above, any compound which effects an increase in the glucuronidation pathway can be an effective substance for the treatment of a hangover and alcohol intoxication. Such substances include, but are not limited to, any salt of glucaric acid (such as calcium, potassium, magnesium, zinc or ferrous salts), or any derivative or metabolized form of glucaric acid (such as glucuronic acid, d-glucaric acid-1,4- lactone, d-glucuronolactone, d-glucurono6,3-lactone, d-glucuronic acid, d-glucuronic acid gamma lactone, and d-glucurone).

The example to follow demonstrates the effectiveness of reducing the overall negative side effects of alcohol consumption as well as supporting evidence to glucarate's role in lowering the total BAC at a higher rate than can be achieved via normal alcohol metabolism.

EXAMPLE

Twenty subjects, currently taking no form of d-glucarate, were recruited for the evaluation. On two separate occasions (at least 5 days apart) the subjects voluntarily consumed alcoholic beverages. The amount ingested was at their discretion, however it was the exact same about on both occasions and roughly over the same duration (+/−½ hour).

On the first occasion, the subject was asked to take a placebo, while on the second occasion the subject was asked to take d-glucarate. The subjects were not informed what they were taking on either occasion, or of the difference between the placebo and chemical compound.

Parameters Taken on Subjects:
Sex
Weight
Alcohol Consumed
Time of consumption
Test Strip Measurement
Administration:

On the first occasion the placebo was administered prior to alcohol ingestion, after alcohol ingestion then 8 hours following ingestion.

A BAC was used to determine the Blood alcohol level after consumption then 8 hours later.

On the second occasion 1000 mg of Potassium Hydrogen Glucarate was administered before alcohol consumption, then 500 mg after alcohol consumption, then 1000 mg 8 hours later.

A BAC test strip was used to determine the Blood alcohol level after consumption then 8 hours later.

Feedback:

The data presented in FIG. 1 indicates, along with the underlying patient data and alcohol consumption, an 18% reduction in the amount of alcohol recirculating within the blood stream immediately after alcohol consumption when administering a glucarate compound relative to a placebo. Upon rest and a duration of 8 hours a more significant decrease in the total level of recirculating alcohol is seen at 55%. This suggests that glucarate has the ability to increase the bodies' ability to remove alcohol more imminently than can be done via the bodies' own natural pathways.

Referring to FIG. 2, 12-14 hours after each occasion the subjects filled out the questionnaire to reflect each subject's observation of hangover symptoms. A 1 on the scale represents the most severe of symptoms, and a 5 represents neutral feeling or no symptom. The black circle indicates the average on the 20 subjects studied.

Referring to FIG. 3, the last parameter measured was the subjects overall feelings, a rating of 1 being the most unpleasant to a rating of 5 representing the most pleasant of each subject's typical feeling.

As can be noted from the data, it appears that the glucarate-administered occurrence produced less of an impact to the overall negative feeling associated with the consumption of alcohol. Within all parameters measured and commented on the average index produced favorable results and reduced the subjects' hangover tendencies.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

We claim:

1. A method for ameliorating at least one symptom of excess ethanol consumption comprising the steps of administering to a human recipient a therapeutically effective amount of an active agent wherein said agent is glucarate or a pharmaceutically acceptable salt, or enantiomer thereof or a derivative thereof selected from a group consisting of d-glucaro-1,4-lactone, d-glucuronolactone, d-glucaro-6,3-lactone, d-glucuronic acid gamma lactone, and d-glucurone and said administering occurring in temporal proximity to the consumption of said ethanol by said human recipient.

2. The method of claim 1 wherein said active agent is selected from a group consisting of calcium glucarate, potassium glucarate, magnesium glucarate, zinc glucarate, and ferrous glucarate.

3. The method of claim 1 wherein said one or more symptoms of excess ethanol consumption is selected from the group consisting of headache, dizziness, nausea, dehydration, fatigue, cotton mouth, stress, bad mood, poor appearance, or poor health.

4. A method for reducing the onset of at least one symptom of excess ethanol consumption, wherein said symptom is included within a group consisting of dizziness, nausea and stress, comprising the steps of administering to a human recipient a therapeutically effective amount of an active agent wherein said agent is glucarate or a pharmaceutically acceptable salt, or enantiomer thereof or a derivative thereof selected from a group consisting of d-glucaro-1,4-lactone, d-glucuronolactone, d-glucaro-6,3-lactone, d-glucuronic acid gamma lactone, and d-glucurone and said administering occurring in temporal proximity to the consumption of said ethanol by said human recipient.

5. The method of claim 1 wherein said symptom is included within a group comprising dizziness, nausea, stress, and pain.

6. The method of claim 4 wherein said active agent is selected from a group consisting of calcium glucarate, potassium glucarate, magnesium glucarate, zinc glucarate, and ferrous glucarate.

* * * * *

UNITED STATES PATENT AND TRADEMARK OFFICE
CERTIFICATE OF CORRECTION

PATENT NO. : 7,662,863 B2  Page 1 of 1
APPLICATION NO. : 10/458764
DATED : February 16, 2010
INVENTOR(S) : Andrews et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 770 days.

Signed and Sealed this

Twenty-eighth Day of December, 2010

David J. Kappos
*Director of the United States Patent and Trademark Office*